(12) United States Patent
Kim et al.

(10) Patent No.: US 6,923,077 B2
(45) Date of Patent: Aug. 2, 2005

(54) APPARATUS AND METHOD FOR WAFER BACKSIDE INSPECTION

(75) Inventors: Dong-Kuk Kim, Chungcheongnam-do (KR); Seung-Bae Jeong, Seoul (KR); Ki-Kwon Jeong, Chungcheongnam-do (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 324 days.

(21) Appl. No.: 10/283,681

(22) Filed: Oct. 29, 2002

(65) Prior Publication Data

US 2003/0159528 A1 Aug. 28, 2003

(30) Foreign Application Priority Data

Feb. 25, 2002  (KR) .......................................... 2002-9878

(51) Int. Cl.[7] .............................................. H01L 21/66
(52) U.S. Cl. ..................................................... 73/865.8
(58) Field of Search ............................ 73/865.8, 865.9; 348/125, 126, 128

(56) References Cited

U.S. PATENT DOCUMENTS

| | | |
|---|---|---|
| 5,422,724 A | 6/1995 | Kinney et al. |
| 5,715,052 A | 2/1998 | Fujino et al. |

FOREIGN PATENT DOCUMENTS

| | | |
|---|---|---|
| JP | 59-032146 | 2/1984 |
| JP | 62-128134 | 6/1987 |
| JP | 09-199560 | 7/1997 |
| JP | 10-092887 | 4/1998 |
| JP | 11-121577 | 4/1999 |
| JP | 2000-097671 | 4/2000 |
| JP | 2000-156391 | 6/2000 |
| KR | 1998-072335 | 11/1998 |
| KR | 1020000014876 | 3/2000 |
| KR | 102000025668 | 5/2000 |
| KR | 1020000025668 | 5/2000 |
| KR | 20-0198268 | 7/2000 |
| KR | 1020000074786 | 12/2000 |
| KR | 2001-0033886 | 4/2001 |

OTHER PUBLICATIONS

20–0198268, Hyundai, Jul. 21, 2000, English language abstract.
102000025668, Samsung Elect., May 6, 2000, English language abstract.
59–032146, NEC Corp., Feb. 21, 1984, English language abstract.
11–121577, MECS Corp., Apr. 30, 1999, English language abstract.
English language abstract of Korean Utility Mode No. 20–0198268.
English language abstract of Korean Patent No. 1020000025668.

(Continued)

*Primary Examiner*—Robert Raevis
(74) *Attorney, Agent, or Firm*—Marger Johnson & McCollom, P.C.

(57) ABSTRACT

An automatic wafer backside inspection may automatically inspect a backside of a semiconductor wafer to look for contamination, cracks, scratches and the like. An inspection apparatus may comprise a wafer cassette with slots to hold a plurality of wafers. A wafer transfer arm may be located near the wafer cassette. A wafer flip/aligner may be operable to flip and align wafers. A wafer inspecting unit may be located adjacent the wafer flip/aligner and be operable to inspect the backside of wafers flipped by the flipper aligner. A wafer buffer stage may be located between the wafer cassette and the wafer flip/aligner for temporarily holding a wafer. The wafer transfer arm may transfer wafers to/from or amongst at least two of the wafer cassette, the wafer flip/aligner, the wafer inspection unit and the wafer buffer stage.

25 Claims, 7 Drawing Sheets

OTHER PUBLICATIONS

English language abstract of Japanese Patent No. 59-032146.
English language abstract of Japanese Patent No. 11-121577.
English language abstract of Korean Publication No. 1998-072335.
English language abstract of Korean Publication No. 2001-0033886.
English language abstract of Korean Publication No. 1020000074786.
English language abstract of Korean Publication No. 1020000014876.
English language abstract of Japanese Publication No. 10-092887.
English language abstract of Japanese Publication No. 62-128134.
English language abstract of Japanese Publication No. 2000-156391.
English language abstract of Japanese Publication No. 2000-097671.
English language abstract of Japanese Publication No. 09-199560.

APPARATUS AND METHOD FOR WAFER BACKSIDE INSPECTION

RELATED APPLICATION

This application claims benefit and priority of Korean Patent Application No. 2002-9878, filed on Feb. 25, 2002, the contents of which are herein incorporated by reference in their entirety.

BACKGROUND

The present invention relates to inspection of semiconductor wafers and in particular to an apparatus and a method to automatically inspect for contamination, cracks, scratches and the like on a backside of a semiconductor wafer.

Conventional manufacture of semiconductor devices may generally be viewed as comprising three processes, i.e., semiconductor wafer fabrication, package assembly and test. The semiconductor wafer fabrication process creates integrated circuits or devices in and on a wafer surface. The wafer fabrication process may be carried out by repetition of many steps such as diffusion, photolithography, thin film formation and etching. After fabrication, the wafer may be sent to a wafer sawing procedure, which may divide the wafer into individual semiconductor chips. Next, each of the individual semiconductor chips may be assembled into a package by package assembly process.

Before the wafer sawing step, the wafer is normally inspected. The inspection generally checks the wafer backside for presence of contamination, cracks, scratches and the like, which may have been introduced during the semiconductor wafer fabrication process. Such contamination or other degradation might damage or adversely affect subsequent processes of the wafer. Conventionally, a wafer backside inspection has been performed manually and inspected visually. For example, an operator may manually grip the wafer and inspect the wafer by the "naked eye."

It may be apparent that such visual inspection may not be reliable because of its dependence on the readiness and availability of the operator. In addition, a lot of time and human resource may be required for such inspection. Furthermore, as manufacturing flows more toward larger diameter wafers, e.g., moving from eight-inch to twelve-inch wafers, a reliability of such visual inspection by operators may drop.

The visual inspection may also be noted to provide an opportunity for recontamination, such as, e.g., scratching of the wafer surface due to inappropriate gripping by an operator.

The visual inspection may present further difficulties when trying to systematically manage the information which may result from the wafer backside inspections. Such information has conventionally been obtained by manually collecting and analyzing the results of the wafer backside inspections. In some instances, a photograph may be taken of the wafer backside. Such manually collected information resulting from the inspections might then be used to adjust some of the upstream procedures of the wafer fabrication process. However, these operations that have been required to collect and return the information to affect the upstream processes have conventionally imposed a heavy burden on the operators.

SUMMARY

In accordance with an embodiment of the present invention, an inspection apparatus may automatically inspect the backside of a semiconductor wafer for contamination, cracks, scratches and the like.

In accordance with one example of such embodiment of the present invention, a wafer backside inspection apparatus comprises a wafer cassette that may contain a plurality of wafers. A wafer transfer arm may be located near the wafer cassette and be operable to transfer a wafer. A wafer flip/aligner may be disposed near the wafer transfer arm and be operable to flip and align the wafer. A wafer inspecting unit may be located near to the wafer flip/aligner and near the wafer transfer arm and be operable to inspect the backside of the wafer. A wafer buffer stage may be located between the wafer cassette and the wafer flip/aligner and be operable to temporarily hold a wafer.

In accordance with a further exemplary embodiment, the wafer flip/aligner may comprise a wafer table to support and align the wafer. A rotator may be operable to grip the wafer placed on the wafer table and move the wafer up to a predetermined height for flipping.

The wafer table may comprise a table body and a plate rotationally coupled thereto. The plate may protrude from the top of the table body and have a diameter smaller than the wafer. The plate may be further operable to apply a vacuum force to the wafer for its securement. The plate may be further operable to rotate the wafer a predetermined rotation for alignment as determined by a sensor formed just outside a peripheral outline of the rotary plate. The sensor may be operable to examine the periphery of the wafer and further operable to detect a flat zone or a notch of the wafer to assist in its alignment.

In a further exemplary embodiment, the rotaror of the flip/aligner may comprise a gripper for gripping the periphery of the wafer. An inverting arm may have one end coupled to the gripper and may be rotationally operable to turn over a wafer gripped therein. A moving guide may be connected to the other end of the inverting arm and may be operable to vertically guide the inverting arm. The moving guide may allow the gripper to move upwardly with a displacement greater than a rotation radius of the gripper.

In another exemplary embodiment, the wafer inspecting unit may comprise a wafer stage operable to receive and support flipped and aligned wafers. A vision module may inspect the upwardly facing backside surface of the wafer placed on the wafer stage. The vision module may have an inspecting camera with a line of sight that is tilted relative to the wafers surface. A focus camera may be located adjacent to the inspecting camera to assist focusing of the inspecting camera. A monitor camera may be located between the inspecting camera and the focus camera and operable to monitor the backside of the wafer being inspected.

A method of wafer backside inspection, in accordance with another exemplary embodiment of the present invention, comprises retrieving a wafer from a cassette containing a plurality of wafers. A first wafer retrieved is transferred from the wafer cassette to a wafer flip/aligner and then flipped to face a backside of the first wafer upwardly. The first wafer may then be transferred from the wafer flip/aligner to a wafer inspecting unit for inspection of the backside. After the backside inspection, the wafer may be re-flipped and sorted.

BRIEF DESCRIPTION OF THE DRAWINGS

Exemplary embodiments of the present invention will be described with reference to the accompanying drawings, wherein like reference numerals designate like structural elements, and, in which.

DETAILED DESCRIPTION

Exemplary embodiments of the present invention will be described below with reference to the accompanying drawings. It will be understood that the depicted elements may be simplified and/or merely exemplary, and may not necessarily be drawn to scale.

Figure 1:
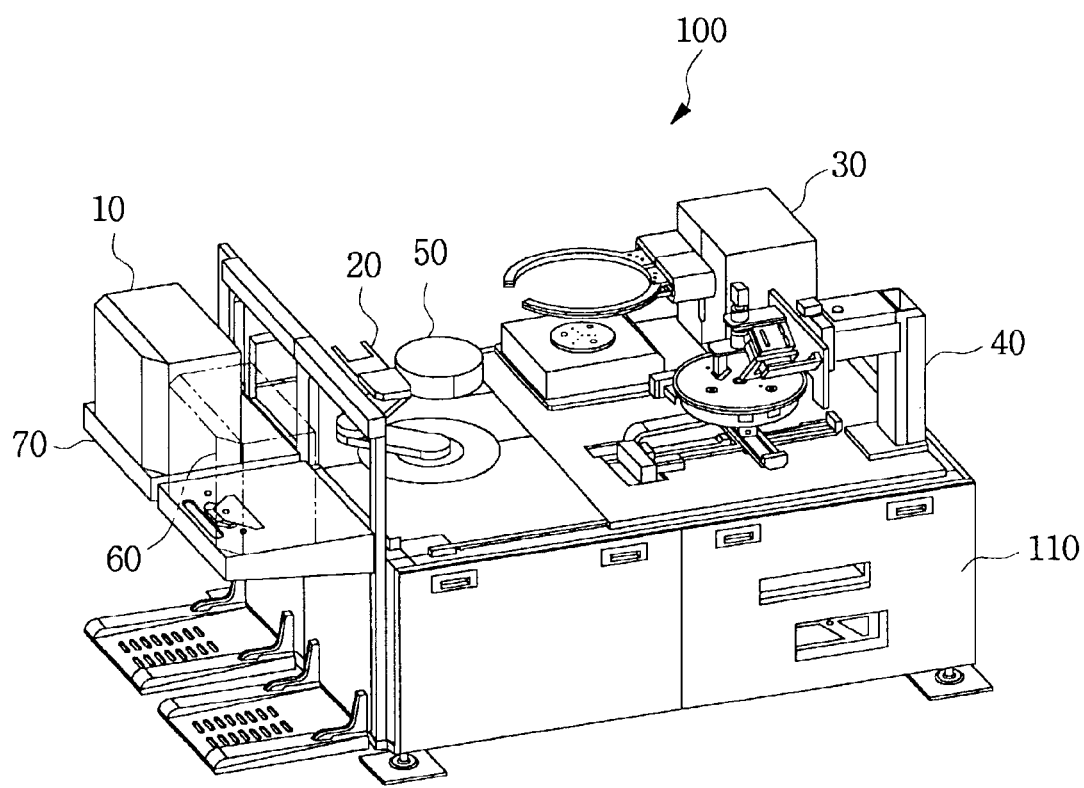
FIG. 1 is a simplified perspective view of a wafer backside inspection apparatus in accordance with one embodiment of the present invention.

FIG. 1 is a simplified perspective view of a wafer backside inspection apparatus in accordance with one exemplary embodiment of the present invention. Referring to FIG. 1, wafer backside inspection apparatus 100 comprises wafer cassette 10, wafer transfer arm 20, wafer flip/aligner 30, wafer inspecting unit 40, wafer buffer stage 50 and defective wafer cassette 60 assembled together on an equipment frame or support structure 110. In this embodiment, wafer cassette 10 and defective wafer cassette 60 may be located side-by-side near one side of wafer transfer arm 20. Wafer flip/aligner 30 and wafer inspecting unit 40 may by disposed side-by-side on the opposite side of wafer transfer arm 20. Wafer cassette 10 and defective wafer cassette 60 may be supported by and fixed on respective cassette support tables 70.

Wafer transfer arm 20 may be operable to transfer a wafer to a desired position by using vertical, horizontal and revolving movements. In this embodiment, the various components of the inspecting apparatus 100 may be located close enough to each other on support structure 110 and to wafer transfer arm 20 so as to enable serviceability by wafer transfer arm 20. In a particular embodiment, the elements are an equal distance from the transfer arm.

Wafer cassette 10 may contain a plurality of wafers, e.g., that may have already been processed by a given wafer fabrication process. The wafers may be loaded into different slots of wafer cassette 10 and with their active surfaces facing upwardly. In this particular embodiment, the wafers that have been determined to pass a backside inspection may be returned to wafer cassette 10.

Figure 3:
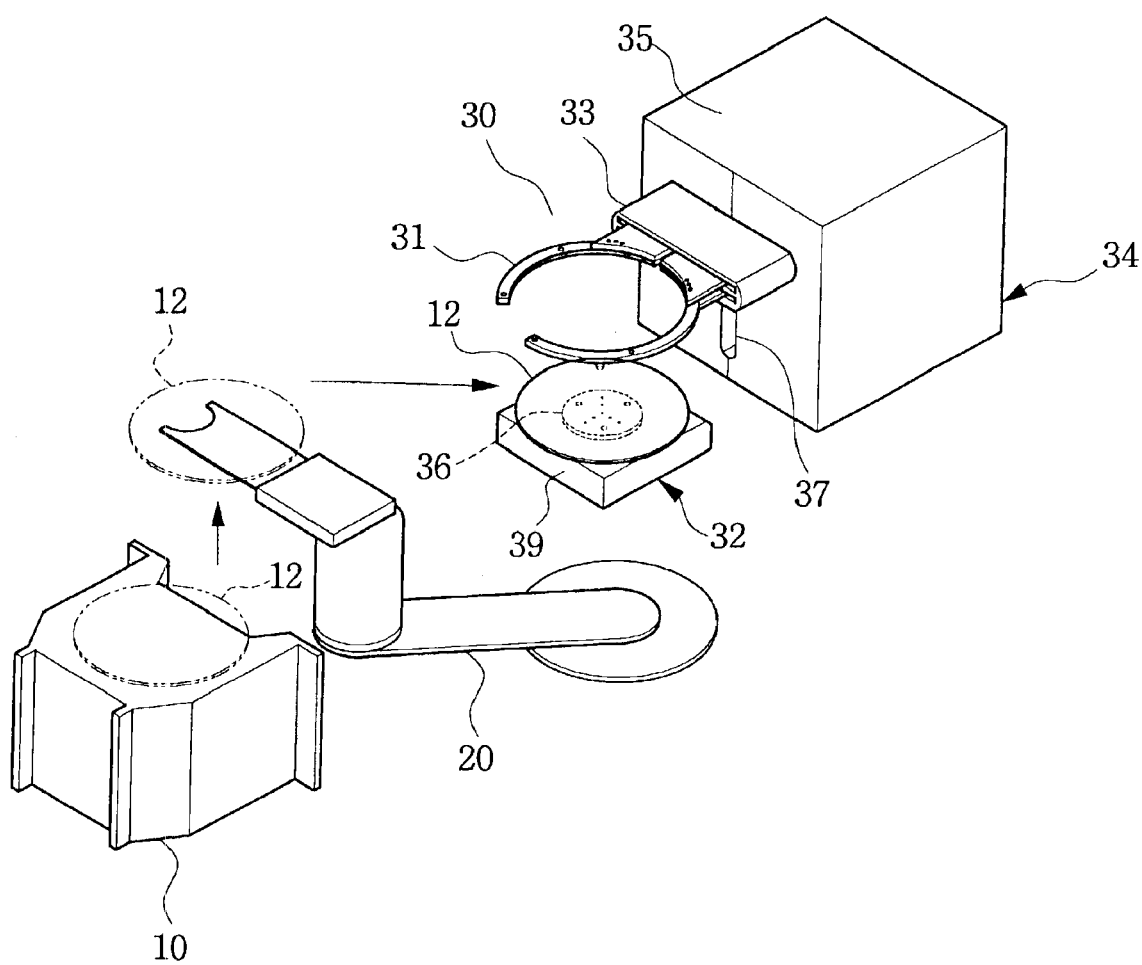
FIG. 3 is a simplified perspective view showing an example of a wafer transfer arm for use in an inspection apparatus and illustrating an exemplary operation of wafer transfer.
Figure 4:
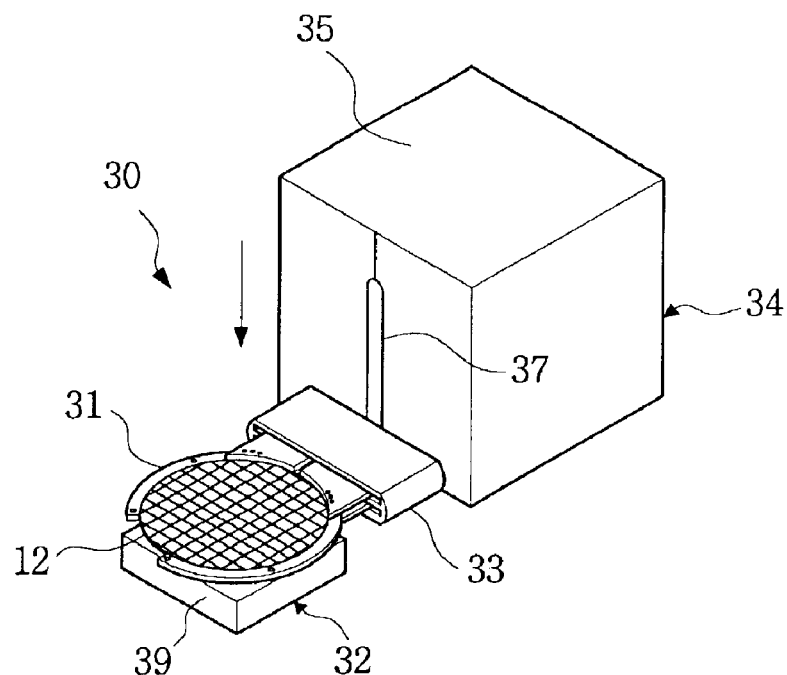
FIGS. 4 to 7 are simplified perspective views showing an example of a wafer flip/aligner for use in an inspection apparatus and illustrating an exemplary operation for flipping a wafer.

Further referencing FIGS. 3 and 4, wafer transfer arm 20 may retrieve a wafer from cassette 10 and may transfer the wafer to a table of flip/aligner 30. Flip/aligner 30 may then flip and align wafer 12 as transferred thereto. In this embodiment, wafer flip/aligner 30 comprises wafer table 32 and rotator 34.

Wafer table 32 may support and fix wafer 12 by use of a vacuum force. Rotator 34 may be operable to flip wafer 12 and then place it back on wafer table 32. Wafer table 32 may comprise table body 39, rotary plate 36 and a sensor (38 of FIG. 5). In this embodiment, plate 36 may protrude the top of table body 39 and comprise a diameter smaller than that of the wafer 12 to be placed thereon. Rotary plate 36 may apply a vacuum force to the wafer for fixing the wafer thereto and to enable rotation to a predetermined position. Sensor 38 may be positioned outside rotary plate 36 and on top of table body 39 for examining the periphery of wafer 12 as will be described subsequently herein.

Further referencing FIGS. 3 through 7, rotator 34 may comprise gripper 31 to grip the wafer placed on rotary plate 36. The rotator may then displace the wafer 12 upwardly from table 32 and may then turn over the wafer 12. In a particular embodiment, rotator 34 comprises a gripper 31, inverting arm 33 and moving guide 35. Moving guide 35 may comprise an elongated guide hole through which inverting arm 33 may be vertically directed. Inverting arm 33 may comprise one end that is connected to moving guide 35 through guide hole 37. Another end may hold gripper 31.

In this embodiment, gripper 31 may comprise a pair of jaws—e.g., disposed as a bisected ring. In this embodiment, the gripper may spread or close-down its jaws to receive and grip a wafer. That is, when wafer 12 is placed on rotary plate 36 of wafer table 32, gripper 31 may move downwardly along moving guide 35 with its jaws spread outward to allow receipt of the wafer. The jaws may then close-down to grip the periphery of the wafer. While gripping the wafer, gripper 31 may then move upwardly as directed by, e.g., a slot 37 of moving guide 35. Moving arm 33 may continue moving upwardly to a predetermined height over the table to a position higher than a rotation radius of gripper 31. Then inverting arm 33 may rotate wafer 12 to an upside down position. After inverting the orientation of wafer 12, gripper 31 may move downwardly along moving guide 25 and may return wafer 12 to rotary plate 36. Rotary plate 36 may support wafer 12 and may secure the wafer thereto by a vacuum force. A rotor may then spin rotational plate 36 to rotate wafer 12 until sensor 38 detects a flat zone or a notch in a periphery of the wafer. Responsive to such detection by the sensor, rotational plate 36 may then fix its position for an alignment of wafer 12.

Figure 9:
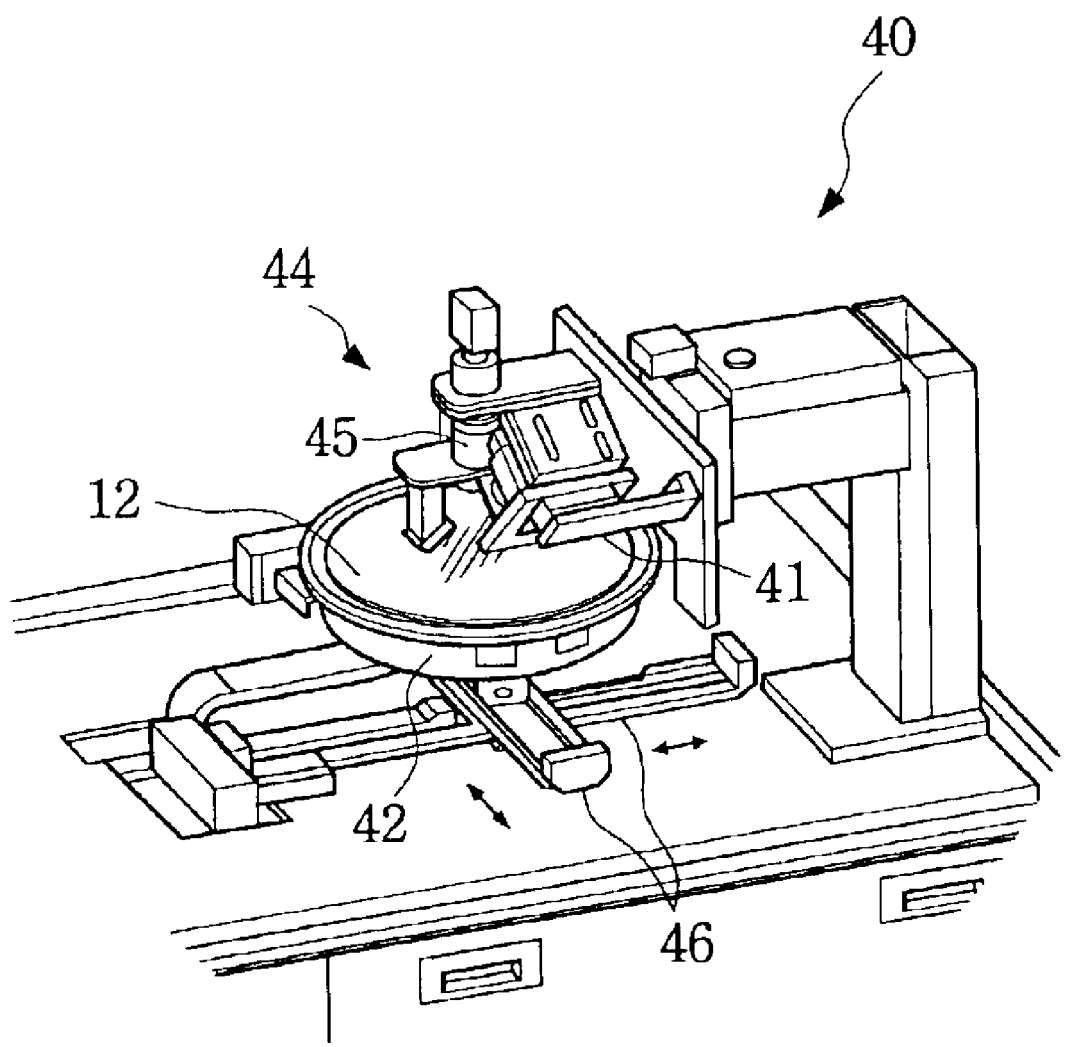
FIG. 9 is a simplified perspective view showing an example of a wafer inspecting unit for use in an inspection apparatus.

After the flipping and alignment of wafer 12, wafer inspecting unit 40, as shown in FIGS. 1 and 9, may inspect the upwardly facing backside surface. Wafer inspecting unit 40, in this embodiment, includes wafer stage 42 and vision module 44.

Wafer stage 42 may support wafer 12 and secure the wafer thereto with a vacuum force. Additionally, the stage may be further operable to move wafer 12 in any direction along rails 46. This free movement of wafer 12 by rails 46 may permit vision module 44 to scan and inspect the entire backside of wafer 12.

Vision module 44 comprises an inspecting camera 41 that may have its line of sight tilted or directed at an angle relative to the upwardly facing backside surface of wafer 12 on wafer stage 42. A focus camera (not shown) may be located adjacent to the inspecting camera 41 and may be used to assist focusing of inspecting camera 41. Additionally, monitor camera 45 may be located between inspecting camera 41 and the focusing camera for monitoring the backside of the wafer 12 being inspected. Image information from inspecting camera 41 may be transmitted to a controller (not shown) of apparatus 100. The controller may then analyze the transmitted image information to determine any contamination, cracks or scratches of the wafer backside for identifying, e.g., a pass or failure condition of wafer 12.

Figure 2:
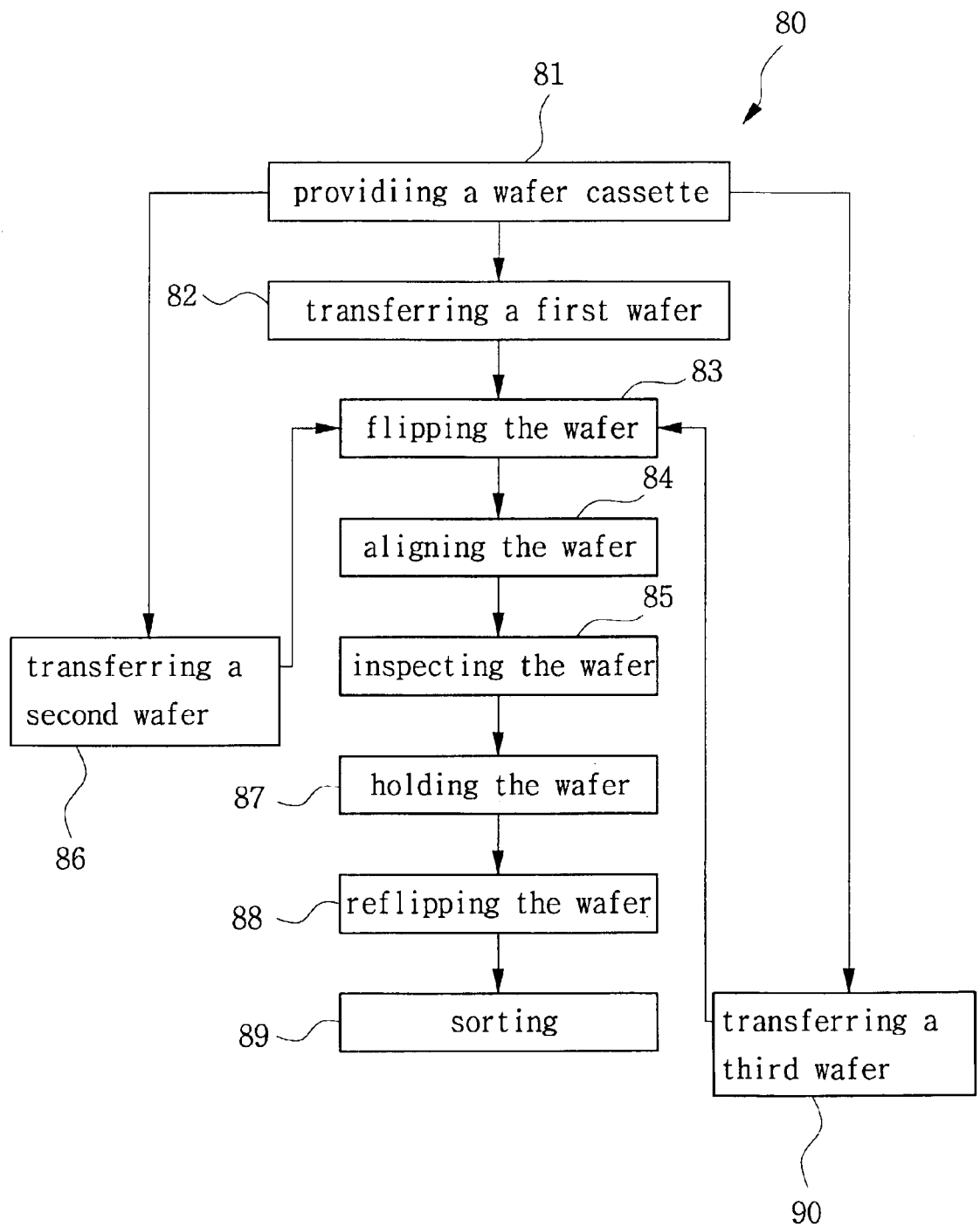
FIG. 2 is a simplified flow diagram useful for explaining a wafer backside inspection method in accordance with another embodiment of the present invention, which may be used with, for example, the apparatus as shown in FIG. 1.

In accordance with a further embodiment, further referencing FIG. 2, wafer buffer stage 50 may temporarily hold the wafer before the inspected wafer is re-flipped by wafer flip/aligner 30. Wafer buffer stage 50, thus, may allow continuous and simultaneous inspection processes for several wafers in a parallel or pipelined fashion, as will be explained more fully subsequently herein.

According to an embodiment of the present invention, when a wafer passes a backside inspection, the wafer may be reloaded into a slot of wafer cassette 10. Conversely, if a wafer fails an inspection, the wafer may be loaded into a defective wafer cassette 60. Such defective wafer cassette 60 may have a structure that is the same as that of wafer cassette 10. In accordance with another embodiment, and alternatively, wafers passing the inspection may be loaded into a new wafer cassette instead of being reloaded into the existing cassette 10.

An exemplary method for wafer backside inspection, which may employ apparatus 100 of FIG. 1, is now described below with reference to FIG. 2. For purposes of convenience and to assist a clear description, continuous and simultaneous inspection processes of the present embodiment may be described with reference to sequential wafers, for example, a first wafer, of a second wafer and a third wafer.

Referring to FIGS. 1 and 2, a method of wafer backside inspection may begin with providing 81 a wafer cassette 10 having a plurality of wafers. Such wafers may have been treated or processed through previous fabrication processes and loaded into, e.g., respective slots of wafer cassette 10 and contained therein with their active surfaces facing upwardly. As used herein, the non-active surface of the wafers opposite the active surface may be described as the "backside" surface.

Continuing with this embodiment, first wafer 12 may be transferred (82 of FIG. 2) to wafer flip/aligner 30 (FIG. 3). For example, wafer transfer arm 20 may retrieve (or unload) the first wafer from wafer cassette 10 and then placed the first wafer onto wafer table 32 of wafer flip/aligner 30.

Figure 5:
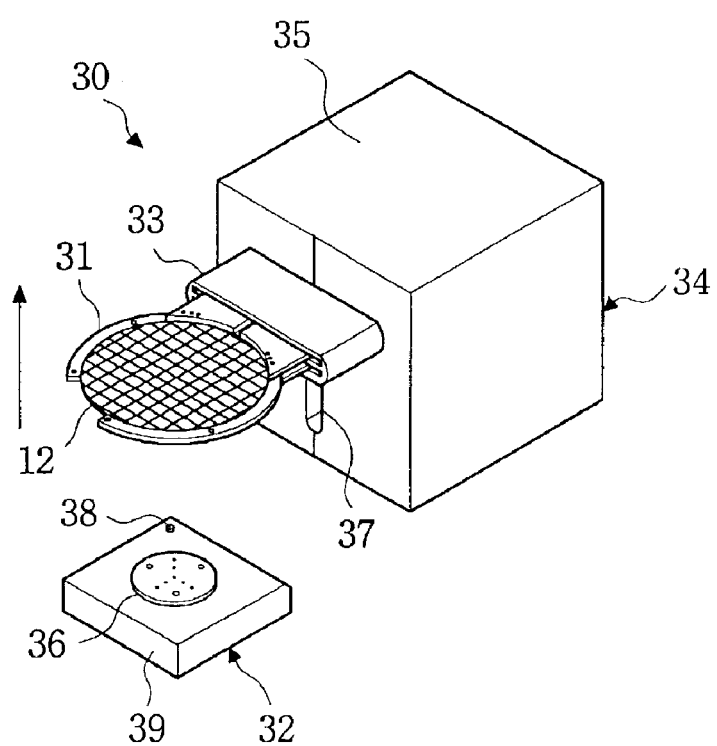
Figure 6:
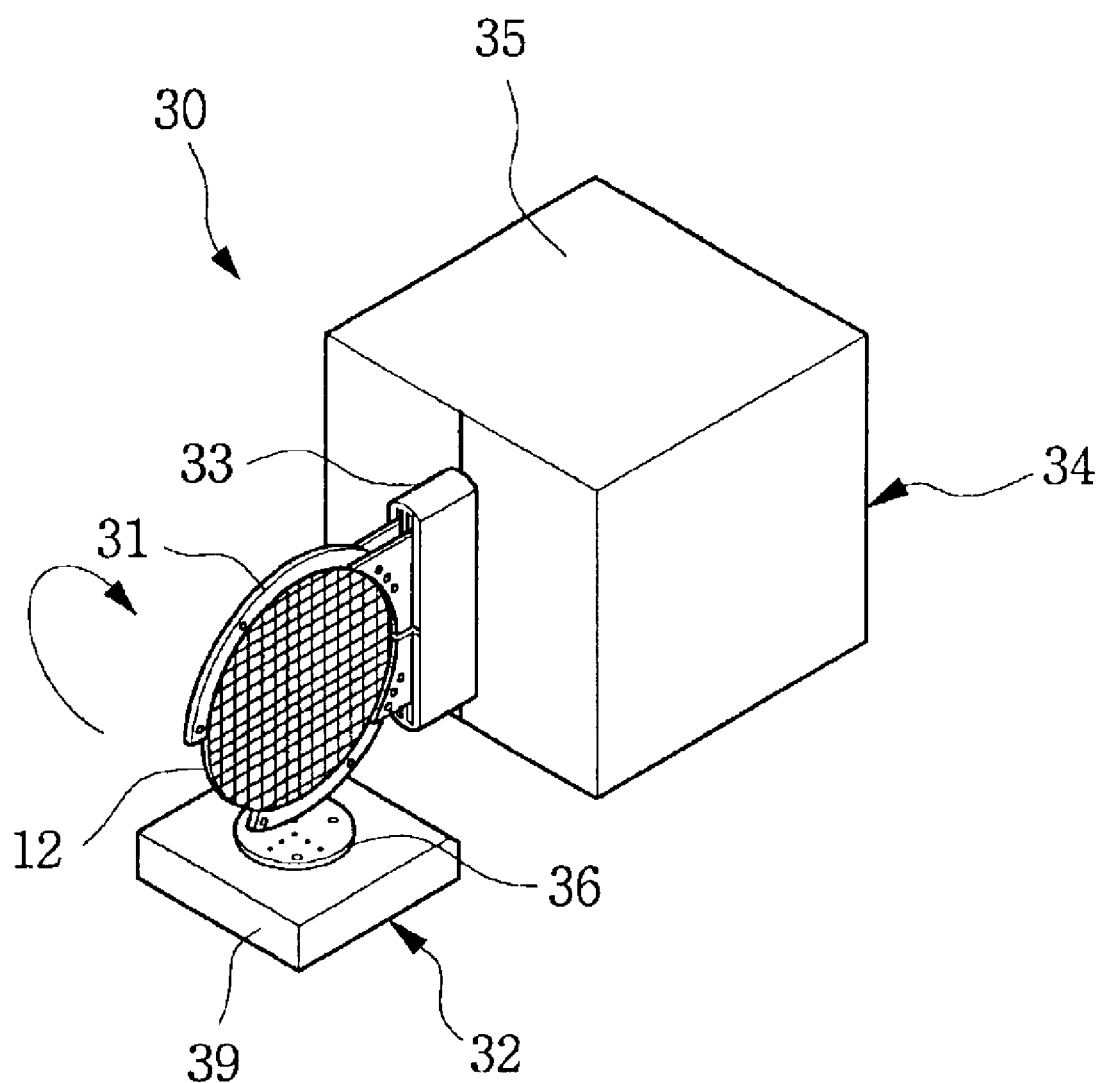
Figure 7:
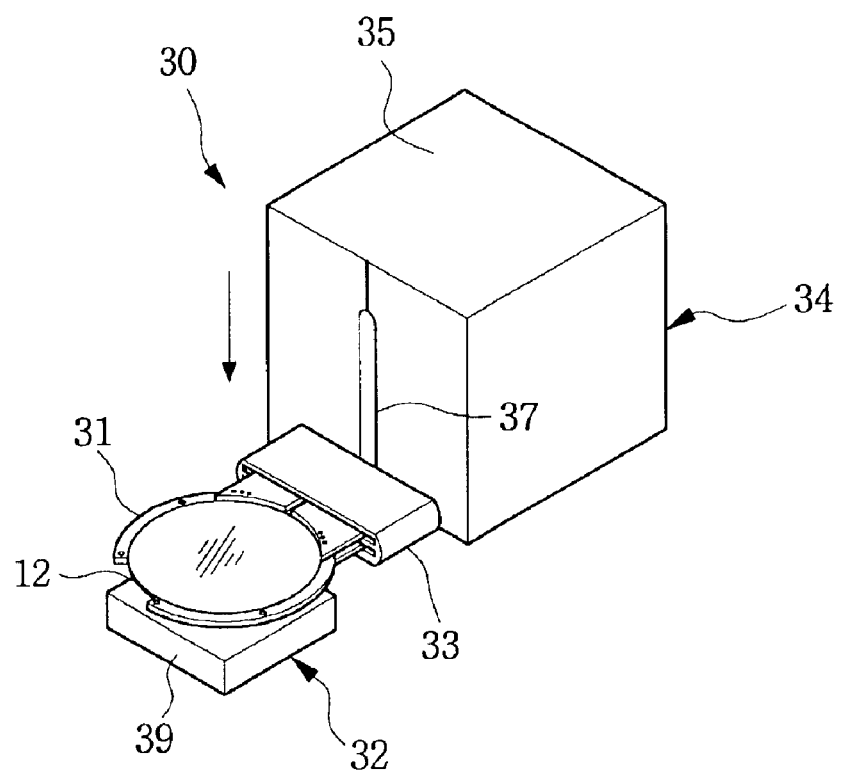

At the flip/aligner, first wafer 12 is flipped (83 of FIG. 2). For example, referencing FIG. 4, once first wafer 12 is placed on wafer table 32, gripper 31 may move down along moving guide 35 of rotator 34 and may close its jaws to grip the periphery of first wafer 12. Then, as shown in FIGS. 5 and 6, while gripping first wafer 12, the gripper may move upwardly along moving guide 35 to a predetermined height above table 32. Inverting arm 33 may then rotate gripper 31 and turn-over wafer 12 such that the backside of first wafer 12 faces upwardly. Referring to FIG. 7, while continuing to grip the overturned first wafer 12, the gripper may move downwardly along moving guide 35 and then place first wafer 12 onto wafer table 32. After releasing the wafer 12, gripper 31 may then be returned to its original position.

Figure 8:
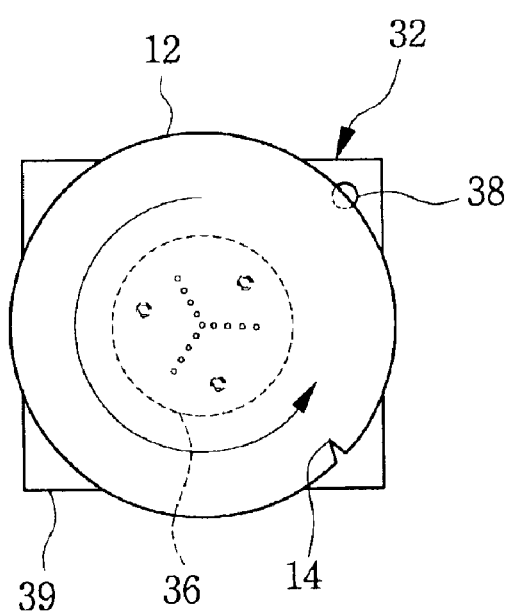
FIG. 8 is a simplified plan view showing an example of an alignment operation for the wafer flip/aligner.

Next, as shown in FIG. 8, first wafer 12 may be aligned (84 of FIG. 2). With the overturned first wafer 12 on rotary plate 36 of wafer table 32, first wafer 12 may be fixed thereto by use of, e.g. a vacuum force. Rotary plate 36 may then rotate the first wafer 12 until sensor 38 identifies, e.g., a flat zone or notch 14. Upon identifying such marking of wafer 12, sensor 38 may signal the rotational plate 36 to fix its position. Accordingly, wafer 12 may be arranged to a predetermined alignment or radial position. Conventional eight-inch or smaller wafers may have a flat zone formed at a given side along their periphery. Alternatively, the wafers may comprise other markings, e.g., such as a notch formed along a periphery thereof. The wafers in this embodiment may be further described herein (as illustrated in FIG. 8) as comprising notch 14.

Further referencing FIG. 9, first wafer 12 may then be sent to a backside inspection (85 of FIG. 2). First wafer 12 may be transferred from wafer table 32 to wafer stage 42 of wafer inspecting unit 40 (e.g., by wafer transfer arm 20). Wafer stage 42 may support and fix first wafer 12 thereto using, e.g., a vacuum force. Rails 46 may guide movement of wafer stage 42 in all directions (e.g., internal and longitudinal directions) along a horizontal plane. Vision module 44 may transmit to the controller image information of the surface (i.e., upwardly facing backside) of first wafer 12. The controller may analyze the image information for determination or detection of possible contamination, cracks, scratches and the like which may be present on the backside of first wafer 12. Subsequently, first wafer 12 may be classified or determined have to passed or failed the inspection based on the analysis of the image information.

In a further exemplary embodiment, during at least a portion of time while first wafer 12 is under inspection, a second wafer may be retrieved from wafer cassette 10 and transferred by wafer transfer arm 20 to wafer flip/aligner 30. The second wafer may then undergo similar flipping and aligning operations by the flip/aligner. After being flipped and aligned, the second wafer may then remain seated at the table of the wafer flip/aligner 30 pending availability of the inspection unit. That is, while the backside of first wafer 12 is being inspected, the second wafer may be flipped and aligned. Such processes, thus, may be termed continuous and simultaneous for respective individual wafers. That is the flipping and aligning operations can be performed (in pipeline fashion) on the second wafer during the backside inspection of the first wafer. Such parallel procedures may allow great efficiency and utilization of inspection apparatus 100 during wafer backside inspections.

Specifically, for a particular exemplary embodiment, the backside inspection of the first wafer might normally require between 1 and 2 minutes, (although the precision of the inspection may make a little difference). At the same time, it may require between a few and ten-odd seconds to transfer a wafer from wafer cassette 10 to wafer flip/aligner 30 and to align the wafer. Thus, these processes may be performed simultaneously and in parallel.

Next, the inspected first wafer may be transferred (87 of FIG. 2) to the wafer buffer stage 50, e.g., by the wafer transfer arm 20. Additionally, the second wafer may be transferred from the wafer flip/aligner 30 to wafer inspecting unit 40.

While the second wafer is being inspected, a series of other steps may be performed. For example, first wafer 12 may be transferred from wafer buffer stage 50 to wafer flip/aligner 30 and may then be re-flipped (89 of FIG. 2). Additionally, the first wafer may be sorted (89 of FIG. 2) according to results of its backside inspection. Upon sorting the first wafer, a third wafer may be transferred (90 of FIG. 2) from wafer cassette 10 to the wafer flip/aligner 30 and then flipped and aligned.

In this embodiment the backside of the first wafer 12 faces upwardly upon completing its backside inspection. Accordingly, the first wafer may be re-flipped just before the sorting so that its front side may face upwardly at its conclusion. The re-flipping may be understood to follow procedures similar to the flipping procedures described earlier herein with reference to FIGS. 4 and 7.

In a particular embodiment, if first wafer 12 is determined to pass, then it may be loaded into wafer cassette 10. In case of determining a failure, the first wafer may be loaded into the defective wafer cassette 60. The third wafer may then be transferred to the wafer flip/aligner 30 to undergo flipping and alignment. After being flipped and aligned at the wafer flip/aligner 30, the third wafer may wait for the availability of next procedure pending transfer of the second wafer to wafer buffer stage 50. Again, the backside inspection may require between 1 and 2 minutes, whereas the re-flipping and sorting of the first wafer 12 and the flipping and aligning of the third wafer may require only a few seconds. Therefore, the re-flipping and sorting of the first wafer and the flipping and aligning of the third wafer might both be performed during the backside inspection of the second wafer.

Likewise, the re-flipping and sorting of the Nth wafer and the flipping and aligning of (N+2)th wafer may similarly be performed during the backside inspection of (N+1)th wafer by the wafer inspection unit 40 (N: natural number). Accordingly, the process may be described as continuous and simultaneous for respective individual wafers. In the context of this description, the Nth wafer may be understood to reference the wafer being re-flipped and sorted; the (N+1)th wafer may be understood to correspond to the wafer undergoing backside inspection in the inspection unit; and the (N+2)th wafer may be understood to correspond to the wafer being flipped and aligned just preceding the inspection.

It may be understood that wafer buffer stage 50 may be simply a stage where an inspected wafer may wait for the availability of its next procedure. Nonetheless, it may be viewed as enabling performance of the various steps of inspection in a continuous manner as disclosed in exemplary embodiments of the present invention. Without wafer buffer stage 50, certain steps might not be available for performance in efficient parallel fashion. For example, the next wafer might not be able to be retrieved, flipped and aligned until after completing the sorting of the first wafer. Specifically, assuming operation without wafer buffer stage 50, transfer of the second wafer to wafer flip/aligner 30 would prevent re-flipping and sorting of the inspected first wafer; the second wafer at wafer flip/aligner 30 would then interfere with re-flipping of the first inspected wafer.

Although exemplary embodiments of the present invention have been described in detail hereinabove, it should be understood that many variations and/or modifications of the basic inventive concepts may appear to those skilled in the art. Such embodiments shall be understood to fall within the spirit and scope of the present invention as defined in the appended claims.

What is claimed is:

1. An apparatus for wafer backside inspection comprising:
    a wafer cassette to contain a plurality of wafers;
    a wafer transfer arm located near the wafer cassette, the wafer transfer arm operable to transfer a wafer;
    a wafer flip/aligner near the wafer transfer arm, the wafer flip/aligner operable to flip and align a wafer;
    a wafer inspecting unit disposed adjacent to the wafer flip/aligner and near the wafer transfer arm, the wafer inspecting unit operable to inspect a backside of a wafer; and
    a wafer buffer stage disposed between the wafer cassette and the wafer flip/aligner for temporarily holding a wafer before the wafer being refined by the flip/aligner.

2. The apparatus of claim 1, in which the wafer flip/aligner comprises:
    a wafer table operable to support and align a wafer; and
    a rotator operable to grip a wafer on the wafer table, displace the wafer relative to the wafer table and flip the wafer.

3. The apparatus of claim 2, in which the wafer table comprises:
    a table body;
    a rotational plate comprising a surface to seat and rotate a wafer over the table body; and
    a sensor to detect a predetermined radial orientation of the wafer on the rotational plate;
    the table body further operable to fix the rotational position of the rotational plate responsive to the sensor detecting the predetermined radial orientation.

4. The apparatus of claim 3, in which the sensor is operable to detect a flat zone or a notch along a peripheral edge of the wafer.

5. The apparatus of claim 3, in which the table body is selectably operable to spin the rotational plate about an axis normal to a wafer's surface.

6. The apparatus of claim 3, in which the rotator comprises:
    a gripper to grip the periphery of the wafer;
    an inverting arm comprising one end secured to the gripper, the inverting arm rotationally operable to turn-over the gripper and the wafer gripped therein; and
    a moving guide connected to the other end of the inverting arm, the moving guide operable to displace the inverting arm relative to the wafer table.

7. The apparatus of claim 6, in which the moving guide is operable to vertically displace the gripper relative the wafer table to a height greater than the rotation radius of the gripper.

8. The apparatus of claim 1, the wafer transfer arm operable to transfer wafers from/to any two of the group consisting of at least the wafer cassette, wafer flip/aligner and wafer inspecting unit.

9. The apparatus of claim 1, in which the wafer inspecting unit comprises:
    a wafer stage to support a wafer; and
    a vision module to inspect a surface of the wafer on the wafer stage.

10. The apparatus of claim 9, in which the vision module comprises:
    an inspecting camera disposed with its line of sight directed at an angle relative to the surface of the wafer;
    a focus camera disposed near the inspecting camera to assist focusing of the inspecting camera; and
    a monitor camera disposed between the inspecting camera and the focus camera to monitor the surface of the wafer.

11. The apparatus of claim 10, in which the inspecting camera is disposed with its line of sight directed toward the surface of the wafer to define an acute angle relative thereto.

12. The apparatus of claim 1, further comprising a defective wafer cassette beside the wafer cassette for receiving defective wafers which fail the backside inspection.

13. A method of inspecting a backside of a wafer, comprising:
    retrieving a first wafer from a wafer cassette;
    transferring a first wafer retrieved by the retrieving to a wafer flip/aligner;

flipping and aligning the first wafer transferred to the wafer flip/aligner and facing a backside of the first wafer upwardly;

after flipping, transferring the first wafer flipped by the flipping to a wafer inspection unit;

inspecting the backside of the first wafer using the wafer inspection unit;

after inspecting, transferring the first wafer to a wafer buffer stage to temporarily hold the first wafer before re-flipping thereof;

after transferring the first wafer to the wafer buffer stage, transferring the first wafer to the wafer flip/aligner; and re-flipping the first wafer and facing the backside of the first wafer downwardly.

14. The method according to claim 13, further comprising:

analyzing results of the inspecting; and sorting the first wafer based upon the analysis of the results.

15. The method of claim 14, further comprising:

during at least a portion of the inspecting the backside of the first wafer, retrieving a second wafer from the wafer cassette, transferring the second wafer to the wafer flip/aligner, and flipping the second wafer to face a backside of the second wafer upwardly.

16. The method of claim 15, further comprising:

during at least a portion of the holding the first wafer on the wafer buffer stage, transferring the second wafer from the wafer flip/aligner to the wafer inspecting unit; and inspecting the backside of the second wafer using the wafer inspecting unit.

17. The method of claim 16, further comprising:

during at least a portion of the inspecting of the second wafer, transferring a third wafer from the wafer cassette to the wafer flip/aligner, and flipping the third wafer to face a backside of the third wafer upwardly.

18. The method of claim 17, in which the sorting of the first wafer is performed during at lead a portion of the inspecting of the second wafer.

19. The method according to claim 14, in which the sorting is performed after the re-flipping.

20. The method according to claim 13, in which the retrieving the first wafer comprises retrieving a wafer from one of a plurality of wafer positions of the wafer cassette.

21. The method of claim 13, in which the transferring and flipping comprise:

using a wafer transfer arm to obtain the first wafer from the wafer cassette and transfer the first wafer to a wafer table of the wafer flip/aligner;

using a gripper to grip the periphery of the first wafer transferred onto the wafer table;

displacing the gripper and the first wafer gripped therein relative to the wafer table;

rotating the gripper and turning the first wafer upside down; and placing the overturned first wafer on the wafer table.

22. The method of claim 21, in which the displacing comprises moving the gripper upwardly.

23. The method according to claim 21, further comprising aligning the first wafer on the wafer table.

24. The method according to claim 23, in which the aligning comprises locating a mark of the first wafer at a predetermined radial position thereof.

25. The method of claim 23, in which the aligning comprises sensing and identifying one of a flat zone or notch along a peripheral edge of the first wafer.

* * * * *

UNITED STATES PATENT AND TRADEMARK OFFICE
CERTIFICATE OF CORRECTION

PATENT NO. : 6,923,077 B2
APPLICATION NO. : 10/283681
DATED : August 2, 2005
INVENTOR(S) : Kim et al.

It is certified that error appears in the above-identified patent and that said Letters Patent is hereby corrected as shown below:

At column 2, line 31, please replace "rotaror" with --rotator--

At column 5, line 4, please replace "placed" with --place--

At columns, line 60 please replace "e.g." with --e.g.,--

At column 6, line 19, please replace "have to" with --to have--

At column 7, line 67, please replace "refined" with --refliped--

At Column 10, line 8, please replace "at lead a portion" with --at least a portion--

In the Drawings Figure 2, please replace "proviiding" with --providing--

Signed and Sealed this

Nineteenth Day of December, 2006

JON W. DUDAS
*Director of the United States Patent and Trademark Office*